United States Patent [19]

Counsell et al.

[11] Patent Number: 4,873,075
[45] Date of Patent: Oct. 10, 1989

[54] POLYIODINATED TRIGLYCERIDE ANALOGS AS RADIOLOGIC AGENTS

[75] Inventors: Raymond E. Counsell; Marc A. Longino; Jamey P. Weichert; Susan P. Schwendner, all of Ann Arbor, Mich.

[73] Assignee: The University of Michigan, Ann Arbor, Mich.

[21] Appl. No.: 774,498

[22] Filed: Sep. 10, 1985

[51] Int. Cl.$^4$ .......................... A61K 49/02; C11C 3/02
[52] U.S. Cl. ................................. 424/1.1; 260/410.7; 560/47; 560/107; 560/106
[58] Field of Search .................. 424/1.1, 9; 260/410.7; 560/47, 107, 106

[56] References Cited

U.S. PATENT DOCUMENTS

| | | | |
|---|---|---|---|
| 3,144,479 | 8/1964 | Obendorf | 260/471 |
| 3,435,066 | 3/1969 | Suter et al. | 260/473 |
| 3,446,837 | 5/1969 | Wallingford | 260/471 |
| 4,192,859 | 3/1980 | Mackaness et al. | 424/5 |
| 4,544,545 | 10/1985 | Ryan et al. | 424/1.1 |
| 4,708,861 | 11/1987 | Popescu et al. | 424/1.1 |

FOREIGN PATENT DOCUMENTS 2451055  5/1975  Fed. Rep. of Germany ....... 424/1.1

OTHER PUBLICATIONS

Abstract No. 29, 186th ACS National Meeting, Division of Medicinal Chemistry, 8/28–9/2/83.
Seevers, et al., Potential Tumor- or Organ-Imaging Agents, 23, Sterol. Esters of Iopanoic Acid, *J. Med. Chem.*, vol. 25, pp. 1500–1053 (1982).
Longino, et al., Biodistribution of a New Lipid-Soluble CT Contrast Agent, *Investigative Radiology*, vol. 18, No. 3, pp. 275–279 (1983).

*Primary Examiner*—John S. Maples
*Attorney, Agent, or Firm*—Rohm & Monsanto

[57] ABSTRACT

Novel iodinated arylaliphatic triglyceride analogs, as radiologic agents are liver and hepatocyte site-specific. The triglyceride backbone structure is preferably 1,3-disubstituted or 1,2,3-trisubstituted with, in some embodiments, a 3-substituted-2,4,6-triiodophenyl aliphatic chain wherein the chain has a structure similar to naturally occurring fatty acids. In another embodiment, a monoiodophenyl aliphatic chain is utilized. Any position remaining on the triglyceride backbone is substituted with a saturated or unsaturated aliphatic hydrocarbon chain of the type found in naturally occurring fatty acids. The triglyceride analogs can be radioiodinated. In a preferred embodiment, a lipid emulsion is provided as the carrier vehicle.

10 Claims, 5 Drawing Sheets 1,3-DISUBSTITUTED TRIGLYCERIDES 1,3-DISUBSTITUTED TRIGLYCERIDES 1,2,3-TRISUBSTITUTED TRIGLYCERIDES

POLYIODINATED TRIGLYCERIDE ANALOGS AS RADIOLOGIC AGENTS

This invention was made with Government support under Contract No. CA-09349 awarded by the Department of Health and Human Services. The Government has certain rights in this invention.

BACKGROUND OF THE INVENTION

This invention relates to polyiodinated compounds useful as radiopaques and radiopharmaceuticals, and more specifically to polyiodinated arylaliphatic triglyceride analogs which are site-specific to the liver and hepatocytes.

The liver is the most common site for the development of metastatic disease, and can be seeded by primary neoplasms of diverse origin, such as the gastrointestinal tract, breasts, lungs, and lymphatics. Although the success of chemotherapy and surgical techniques has improved the prognosis of affected patients, it is known that reliable and early detection of the liver metastases is required if therapeutic measures are to be effective. Thus, early detection of small metastatic lesions has been a long-term goal of radiology and nuclear medicine.

Over the past several decades, significant advances have been made in systems which enable visualization of internal organs, such as the liver, by noninvasive procedures. Two of the most widely used imaging modalities, radiography and radioisotope scanning, owe much of their success to the development of suitable radiopaques and radiopharmaceuticals. A major pharmacological difference between radiopaques and radiopharmaceuticals is that large doses of the former are required for opacification of soft tissue, whereas the latter are administered in tracer doses. The advent of computed tomography (CT), however, now offers the possibility of reducing this dosage differential. In contrast to conventional-X-ray imaging which reliably detects differences in tissue density of 5–10%, CT can detect differences as small as 0.5%.

Although X-ray CT using water-soluble, urographic contrast agents is currently the most accurate, noninvasive radiologic examination routinely used for the evaluation of hepatic masses, this imaging modality has definite limitations in the detection of lesions smaller than 2 cm. The major limitation is due largely to the rapid egress of the urographic agents from the vascular system into the extracellular spaces, thus reducing the contrast differential between the tumor and the normal liver tissue. Indeed, since many metastatic lesions would be smaller than 2 cm in patients with incipient liver disease, it is imperative that contrast agents specifically localize within the normal cells of the liver, and remain there for a sufficiently long period of time to enable high quality images to be obtained by CT. Thus, there is a need for liver-specific contrast agents for CT which possess the target organ specificity that the urographic agents lack. Moreover, the urographic agents achieve liver enhancement by uptake by the reticuloendothelial (RE) system. However, the majority of metastases involve primarily liver hepatocytes, and therefore the efficacy of RE-specific agents for CT detection of small hepatic matastases is limited. Thus, there is also a need for hepatocyte selective agents.

Alternatives to the urographic agents currently in wide-spread use have been evaluated for greater organ selectivity and longer duration of contrast enhancement. These agents include ethiodized oil emulsions (EOE 13), radiopaque liposomes, iodinated starch particles, and iodipamide ethyl ester. As is the case with urographic agents, these agents have had only limited success, at least partially as a result of the fact that they operate by uptake into the RE system.

Iodine has played an important role in radiopaque and radiopharmaceutical diagnostic compositions, such as those referenced above. Iodine not only imparts the necessary electron density to radiopaques; but can, in its various isotope states (e.g., $I^{123}$, $I^{125}$, and $I^{131}$), emit the gamma radiation essential for gamma-camera scintigraphy. Currently, however, the most widely used liver scintigraphy agent is $^{99m}$Tc-sulfur colloid. This agent is removed from the circulation by phagocytic action of RE cells. The static anatomic image thus obtained proves useful in the location of primary and secondary lesions as small as 2–3 cm in diameter, but has no utility in assessing hepatocyte function. Hepatocyte function can, however, be studied by monitoring the uptake and clearance of $^{131}$I-Rose Bengal (tetraiodotetrachlorofluorescein), a dye which is extracted by hepatocytes and, under normal conditions, is quickly secreted into the bile. This agent, however, is disadvantageously characterized by a slow rate of hepatic to intestinal output, poor imaging characteristics, and high radiation doses associated with $^{131}$I. Consequently, there is a need for both a hepatocyte-specific scintigraphy agent and a liver-specific CT agent.

It is, therefore, an object of the invention to provide improved radiologic agents which are liver specific for CT purposes and hepatocyte selective for scintigraphy purposes.

It is another object of the invention to provide improved radiologic agents which are liver specific and will reveal metastatic lesions smaller than 2 cm.

It is a further object of the invention to provide improved radiologic agents which are hepatocyte selective rather than reticuloendothelial system selective.

It is also an object of the invention to provide improved radiologic agents which will opacify soft tissue when administered in small doses.

It is an additional object of the invention to provide radiologic agents which will be physiologically acceptable and non-toxic.

It is still another object of the invention to provide improved radiologic agents which will remain in the target organs for residence periods of sufficient duration to enable high quality imaging.

It is yet another object of the invention to provide techniques for producing such improved radiologic agents.

It is additionally an object of the invention to provide iodine-containing radiologic agents which can be used as radiopaques, or which can be radio-tagged for use in scintigraphy.

It is yet another object of the invention to provide an improved technique for producing radio-tagged scintigraphy agents.

It is a yet further object of the invention to provide improved radiologic agents which are subject to hydrolysis and deiodination so that the radiologic agents will be cleared from the body of the patient to whom the radiologic agent has been administion within a reasonable period of time; but which will be stable enough to permit adequate residence time for good imaging by CT.

It is additionally a further object of the invention to provide an improved carrier vehicle for the radiologic agents which is site-specific and lipid-based.

It is still a further object of the invention to provide an improved technique for incorporating a radiologic agent in a lipid-based carrier vehicle.

It is yet a still further object of the invention to provide a radiologic agent/vehicle formulation which is isotonic and avoids the patient discomfort accompanying hyperosmolarity.

SUMMARY OF THE INVENTION

The foregoing and other objects are achieved by this invention which provides a novel iodinated arylaliphatic triglyceride compound of the general formula:

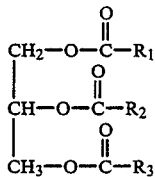

$R_1$, $R_2$, and $R_3$ are selectably a saturated or unsaturated aliphatic hydrocarbon chain of the type found in naturally occurring fatty acids or a 3-substituted-2,4,6-triiodophenyl aliphatic chain. In preferred embodiments of the invention, $R_1$ and $R_3$ are 3-substituted-2,4,6-triiodophenyl aliphatic chains, thereby forming 1,3-disubstituted triglyceride, and $R_1$, $R_2$, and $R_3$ are 3-substituted-2,4,6-triiodophenyl aliphatic chains, thereby forming 1,2,3-trisubstituted triglyceride.

The 3-substituted-2,4,6-triiodophenyl aliphatic chains have the general formula:

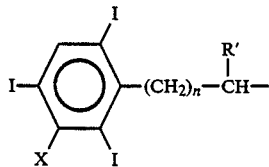

In preferred embodiments of the invention, X is hydrogen, an amino or an acetamido (NHCOR", where R" is a lower alkyl) substituent. R' is either a hydrogen or a lower alkyl substituent and n is an integer from 0 to 15. Thus, the branch chain on the 3-substituted-2,4-6-triiodophenyl aliphatic chain forming the linkage with a carbonyl on the triglyceride backbone resembles the saturated or unsaturated aliphatic hydrocarbon chains found in naturally occurring fatty acids.

In another embodiment of the invention, at least some of the iodines in the triglyceride compound are radioactive. In the radioactive embodiment, a 3-substituted-monoiodophenyl aliphatic chain, having iodine at any position, can be used instead of the 3-substituted-2,4,6-triiodophenyl aliphatic chain.

The polyiodinated arylaliphatic triglyceride compounds of the instant invention are useful as radiologic agents. As used herein the term radiologic agents refers to both radiopaques and radiopharmaceuticals. As radiologic agents, the polyiodinated triglyceride analogs are liver-specific and hepatocyte-selective. As a radiopaque, the novel compounds find particular applicability as a contrast agent for computed tomography. In the radio-iodinated form, the novel compounds find particular applicability as a hepatocyte-specific scintigraphy agent.

In an advantageous embodiment of the invention, the novel radiologic agents are incorporated into a lipid emulsion as a site-specific carrier vehicle. The lipid emulsion comprises a lipid core containing, inter alia, triglycerides, surrounded by a phospholipid monolayer. In specific illustrative embodiments, the lipid emulsion contains about 10% by weight of a combination of the novel polyiodinated triglyceride analog and a naturally occuring triglyceride per volume of the lipid emulsion. The phospholipid monolayer comprises phosphatidyl choline, and in certain embodiments, traces of a sterol stabilizer, such as cholesterol.

DETAILED DESCRIPTION OF THE INVENTION

Figure 1:
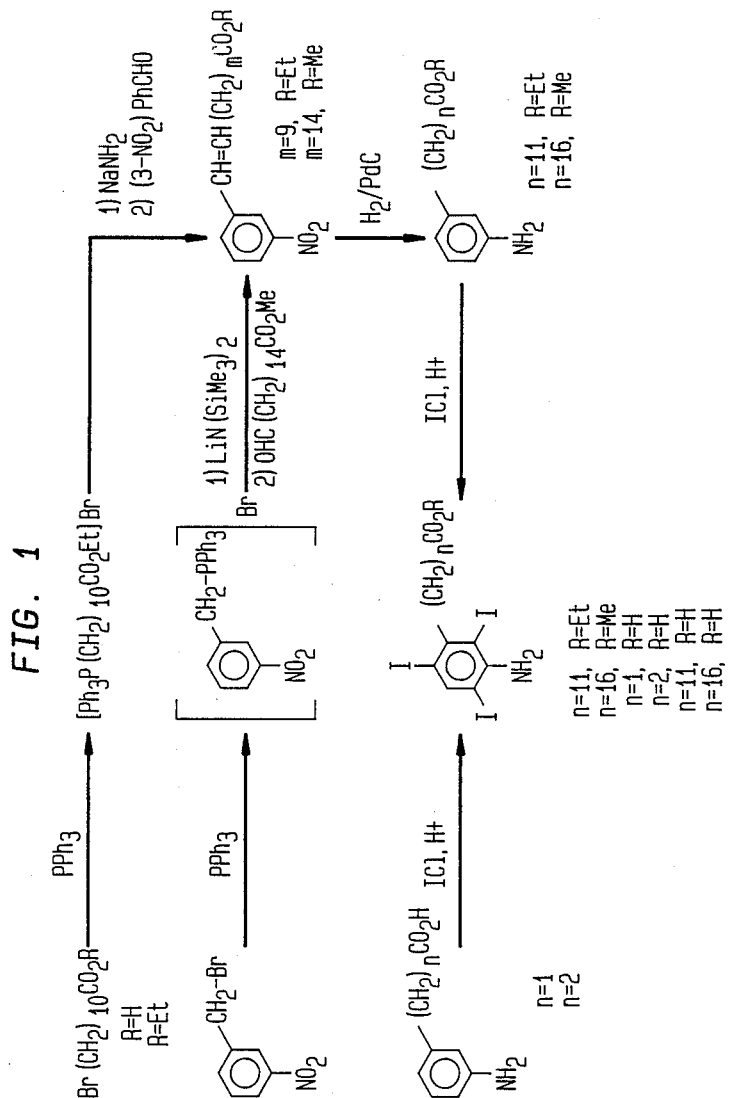
FIG. 1 is a flow chart of two schemes for the synthesis of ω-(3-amino-2,4,6-triiodophenyl)-alkanoic acids.

The novel compounds of the instant invention are polyiodinated triglyceride analogs of naturally occurring substances having the basic formula:

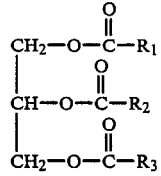

wherein the glyceride backbone is preferably di-substituted ($R_1$ and $R_3$) or tri-substituted ($R_1$, $R_2$, and $R_3$) with 3-substituted-2,4,6-triiodophenyls of the general formula:

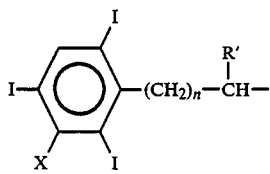

wherein X is illustratively $NH_2$, H, or $NHCOCH_3$ or another NHCOR" wherein R" is a lower alkyl. The 3-position substituent (X) modifies the toxicity of the compound and, in addition to those specifically named herein, can include other known amino-substituents, or even hydrogen, which are commonly used in the preparation of radiologic agents to modify toxicity. Of course, the di-substituted $R_2$ and $R_3$ or $R_1$ and $R_2$ isomers are included within the general formula of the novel compounds; however, these isomers would be unsymmetrical, resulting in D and L racemates.

The remaining, if any, substituent position of the glyceride backbone can be any saturated or unsaturated aliphatic hydrocarbon chain of the type found in naturally occurring fatty acids. Examples of naturally occurring fatty acids on which this chain can be based are myristic acid, palmitic acid, stearic acid, linoleic acid, arachidonic acid, and oleic acid. As can be seen from the general formula for the 3-substituted-2,4,6-triiodophenyl shown above, the branch chain linking the phenyl radical to a carbonyl on the glyceride backbone can be a fatty acid-like hydrocarbon chain also. Specific illustrative embodiments of the novel compounds of the invention herein will be described in detail hereinbelow.

The site-specific delivery of the polyiodinated triglyceride analogs of the invention herein is based on exploitation of the mammalian triglyceride transport and uptake processes to deliver the agents selectively to the liver or hepatic cells. Unlike the water-soluble contrast agents commonly used in the prior art, or known lipid-soluble contrast agents such as ethiodized oil, the polyiodinated triglyceride analogs are hepatocyte-specific rather than reticuloendothelial cell (Kupffer cell)-specific. Thus, the polyiodinated triglycerides are effective contrast enhancers for hepatic lesions even smaller than 2 cm. The high degree of site specificity obtained with the triglyceride analogs herein has the advantage of reducing the total body dose of iodine required for imaging.

In a preferred embodiment of the invention, which will be discussed in greater detail hereinbelow, the lipid-soluble nature of the polyiodinated triglyceride analogs enables them to be incorporated in a fat emulsion, similar to the endogeneus chylomicrons, which are rapidly sequestered by the hepatocyte liver cells, as a delivery vehicle for the intravenous injection of the agents to a mammal. Thus, the combination of the polyiodinated triglyceride analogs and a chylomicron-like lipid emulsion carrier vehicle produces an extremely effective target-specific radiologic agent.

As is known, chylomicrons are responsible for the transport of dietary or exogenous lipids in the circulation. Lipids such as cholesterol and triglycerides are absorbed from the intestinal tract by mucosal cells and are incorporated into chylomicrons which are substantially secreted into and transported through the lymphatics until they reach the circulation via the thoracic duct. Once in circulation, the chylomicrons are metabolized by peripheral tissue lipoprotein lipase which hydrolyzes the entrapped triglycerides, thereby liberating free fatty acids which can then be utilized in cell metabolism. The remaining cholesteryl ester-rich, triglyceride-deficient chylomicron, called chylomicron remnants, are then cleared very rapidly from the circulation by the liver via a receptor-mediated process.

Based on the finding that peripheral lipoprotein lipase is known to hydrolyze glyceryl esters preferentially at the 1- and 3-positions prior to cleavage of the 2-ester group, 2-monosubstituted polyiodinated triglycerides were prepared and tested for efficacy as a site specific radiologic agent. It was surprisingly discovered, however, that the mono-substituted triglyceride analogs are not characterized with the advantageous specificity for the liver that di- and tri-substituted triglycerides have. Moreover, the mono-substituted compounds do not have as large an iodine concentration per mole as the di- and tri-; and therefore do not achieve the same level of radiopacity. The mono-substituted triglyceride analogs are also more rapidly hydrolyzed, and thus, are not retained in the target organ for as long a period of time.

Methods of synthesizing the polyiodinated triglyceride analogs begin with the preparation of the desired polyiodinated alkanoic acid of the general formula:

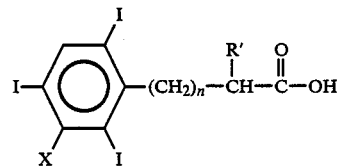

wherein x is $NH_2$, H, or $NHCOR''$, $R''$ being a lower alkyl; $R'$ is H or a lower alkyl; and n is an integer from 0 to 15. For the radioactive embodiments using 3-substituted-monoiodophenyl chains, an iodophenyl alkanoic acid is prepared.

PREPARATION OF IODINATED ALKANOIC ACIDS

In specific illustrative embodiments, two methods for preparing ω-(3-amino-2,4,6-triiodophenyl) alkanoic acids are described hereinbelow. While the exemplary embodiments herein are directed toward synthesis of polyiodinated alkanoic acids wherein the 3-position (or X) is $NH_2$, analogs wherein the 3-position is $NHCOR''$ can be synthesized, for example, by acetylation of the amino-substituted analog.

Method A

Reference to FIG. 1 shows the reaction sequence for Method A and Method B, to be discussed hereinbelow, in flow chart format.

Method A basically comprises catalytic hydrogenation of a 3-nitrophenyl alkanoic acids with subsequent iodination of the resulting 3-aminophenyl alkanoic acid.

EXAMPLE 1

3-Aminophenylacetic acid was prepared from a solution of 3-nitrophenylacetic acid (5.08 g, 28 mmol) in absolute ethanol (100 ml) which was hydrogenated at 40° C. and 40 psi in the presence of 5% Pd/C catalyst for 3 hours. The catalyst was removed by filtration, and upon removal of the solvent in vacuo, a highly viscous yellow oil remained which resisted crystallization.

A solution of 3-aminophenylacetic acid was prepared by mixing 3.8 g (25 mmol) of the acid in 200 ml water and 10 ml concentrated HCl. This solution was warmed to 75° C. in a 3-necked flask equipped with a condenser and mechanical stirrer, and was subjected to a solution of ICl (14.3 g, 88 mmol) in concentrated HCl (35 ml). The reaction mixture was stirred for three hours, cooled to room temperature, and filtered. A brown filter cake, thus obtained, was throughly washed with water, transferred to a flask, and treated with excess NaOH (1.0 g) and heated to 80° C. on a steam bath. An additional 70 ml of water was added to aid dissolution and the resulting solution was heated for 30 min. and cooled to room temperature. The sodium salt was filtered, washed with cold water, and then dissolved in about 250 ml of 1% sodium bisulfite with heating to about 80° C. After about 15 minutes, the solution was acidified with 8 N HCl (pH 4-5 on litmus) and slowly cooled to 5° C. The large off-white plates of 3-amino-2,4,6-triiodophenylacetic acid which were formed were filtered, washed with cold water, and dried under vacuum overnight at a temperature of 100° C.

EXAMPLE 2

3-Aminohydrocinnamic acid was prepared by hydrogenating 3-nitrocinnamic acid in a similar procedure as Example 1. 10.7 g (55 mmol) of 3-nitrocinnamic acid was dissolved with heating in 300 ml of absolute ethanol and reacted at 50° C. and 50 psi in the presence of 1.5 g 5% Pd/C catalyst for 1 hour. Filtration and subsequent solvent evaporation yielded a viscous yellow liquid which was 3-aminohydrocinnamic acid.

A solution of 6.0 g (36 mmol) 3-aminohydrocinnamic acid in 300 ml water and 10 ml conc. HCl was treated with a solution of 20.6 g (127 mmol) ICl in 50 ml conc. HCl and stirred for 3 hours to form crude iodinated acid. The acid was converted to its sodium salt upon treatment with 1.5 g NaOH, was crystallized, and precipitated from 1% aqueous sodium bisulfite in the manner described in Example 1. The desired acid was collected by filtration, washed with water, and dried under vacuum at 100° C. overnight. The resultant product was 3-amino-2,4,6-triiodophenylpropionic acid.

Method B

The starting material for the preparatory scheme of Method B is a ω-bromoalkanoic acid. A phosphonium salt of the ω-bromoalkanoic acid is prepared and converted into the corresponding ω-carbethoxyalkylidine triphenyl phosphoran with sodium amide. The ω-carbethoxyalkylidinetriphenylphosphonium salt is converted to a nitrophenyl-alkenoate by a Wittig condensation of 3-nitrobenzaldehyde. Catalytic hydrogenation reduces the nitrophenyl-alkenoate to aminophenyl alkanoate. The alkanoate is iodinated and hydrolyzed to the aminophenyl alkanoic acid.

EXAMPLE 3

In this example, 12-(3-amino-2,4,6-triiodophenyl)-dodecanoic acid is synthesized. 11-Bromoundecanoic acid (54.0 g, 200 mmol) was refluxed overnight with 150 ml absolute ethanol and a catalytic amount (1.0 ml) $H_2SO_4$. The solvent was removed in vacuo and the residue was dissolved in 100 ml CHCl and extracted with 100 ml $H_2O$, twice with 100 ml 10% aq. $NaHCO_3$, 100 ml water, and brine, and was dried with $MgSO_4$ Removal of the solvent in vacuo and distillation of the remaining yellow liquid under vacuum yielded ethyl-11-bromoundecanoate as a colorless liquid.

The ethyl-11-bromoundecanoate (54.0 g, 184 mmol) was dissolved in 150 ml of acetonitrile. 53.1 g (203 mmol) of triphenylphosphine was added to the solution and the resulting mixture was heated at reflux for 36 hours under nitrogen. The reaction mixture was cooled, and the solvent removed in vacuo. The syrup-like residue was triturated with anhydrous ether to remove any remaining triphenylphosphine. The result was ω-carbethoxyundecylidenetriphenylphosphonium bromide salt.

53.0 g (95 mmol) of the bromide salt was dissolved in 100 ml of dry THF. A suspension of $NaNH_2$ (4.11 g, 105 mmol) in 20 -ml of anhydrous THF was cooled to 5° C. and treated with the bromide salt solution. After 30 minutes, a solution of 3-nitrobenzaldehyde (13.2 g, 87 mmol) in 20 ml dry THF was added dropwise to the bromide salt solution and the resulting mixture was stirred for 12 hours at room temperature under nitrogen. The heterogenous mixture resulting from this step was then filtered to remove NaBr and the solvent was removed in vacuo. The residue was dissolved in an ether/$H_2O$ (1:1) mixture and the layers were permitted to separate. The organic layer was washed successively with $H_2O$, 2% aq. sodium bisulfite, $H_2O$, brine, and then dried with $MgSO_4$. The solvent was removed in vacuo and the residue triturated with anhydrous ether to precipitate any final traces of triphenylphosphine oxide. Filtration and concentration of the filtrate in vacuo afforded a yellow liquid which was purified by column chromatography on silica gel eluted with hexane/ether (3:2). The result was ethyl 12-(3-nitrophenyl)-11-dodecenoate.

The ethyl 12-(3-nitrophenyl) 11-dodecenoate was reduced to the corresponding nitroalkanoate ester by hydrogenation of a solution of 11.2 g (32 mmol) in 150 ml of absolute ethanol in the presence of 1.5 g 5% Pd/C catalyst at room temperature and 50 psi for 2 hours. The catalyst was removed by filtration through a pad of celite, and upon removal of solvent in vacuo. a colorless homogenous liquid which was ethyl 12-(3-aminophenyl)-dodecanoate remained.

The ethyl 12-(3-aminophenyl)-dodecanoate was iodinated in a manner similar to that set out in Example 1. A solution of 16.2 g (100 mmol) ICl in 100 ml $CHCl_3$ and 50 ml 8 N HCl was heated to 70° C. in a 3-necked flask equipped with a reflux condenser, an addition funnel, and a mechanical stirrer. A solution of 8.0 g ethyl-(3-aminophenyl)-dodecanoate in 30 ml $CHCl_3$ was added dropwise to the ICl solution and the resulting biphasic mixture was stirred for 3 hours. The reaction mixture was allowed to cool to room temperature, the layers were separated, and the aqueous phase was extracted twice with $CHCl_3$. The combined $CHCl_3$ layers were washed successively with water twice, 10% aq. $NaS_2O_3$, water, and brine, and then dried with $MgSO_4$. Upon removal of the solvent in vacuo, a red liquid remained which crystallized upon standing. Recrystallization from methanol/$CHCl_3$ gave fine silvery needles of ethyl 12-(3-amino-2,4,6-triiodophenyl)-dodecanoate.

The triiodinated ester (9.7 g, 13.9 mmol) was dissolved in 40 ml of THF and 100 ml of 95% ethanol and treated with 1.5 g of NaOH. The resulting mixture was refluxed for 3 hours, acidified with 1 N $H_2SO_4$ (pH 4–5 on litmus), and diluted with 200 ml $CHCl_3$. The layers were separated and the aqueous layer was extracted with $CHCl_3$. The organic layer was washed with water twice then, brine, and dried with $MgSO_4$. The solvent was removed in vacuo and the crude product was recrystallized from methanol/$CHCl_3$ to give off-white needles of 12-(3-amino-2,4,6-triiodophenyl)-dodecanoic acid.

EXAMPLE 4

Methyl 17-(3-nitrophenyl)-16-heptadecenoate was synthesized from 3-nitrobenzyl bromide according to the reaction sequence shown in the middle of FIG. 1. A mixture of 38.7 g (179 mmol) 3-nitrobenzyl bromide and triphenylphosphine (51.6. g, 197 mmol) in dry benzene (200 ml) was refluxed under nitrogen for 18 hours. The reaction mixture was cooled to room temperature and filtered to collect the phosphonium salt, 3-nitrobenzyl-triphenylphosphonium bromide. The salt was washed with copious amounts of anhydrous ether to remove any remaining triphenylphosphine. The remaining white powder was dried in vacuo.

A stirred suspension of 19.17 g (40 mmol) of the phosphonium salt in 60 ml anhydrous THF was cooled to 0° C. under $N_2$ and treated by dropwise addition with a solution of 44 ml of a 1.0 M solution of lithium bistrimethylsilylamide in anhydrous THF. After 20 minutes, a solution of 9.5 g (33 mmol) of methyl 16-oxohexadecanoate in 50 ml dry THF was added slowly via syringe over a period of 10 minutes. The reaction mixture was allowed to warm to room temperature and was stirred under $N_2$ for 14 hours, at which time no aldehyde was present as determined by TLC. Most of the solvent was removed in vacuo and the remaining reaction mixture was diluted with a mixture of ether and water (150 ml:100 ml). The layers were separated and the aqueous layer was extracted with ether. The ether layers were combined and washed with 0.5 N HCl, 10% aq. $NaHCO_3$, $H_2O$, and brine and dried with $MgSO_4$. The solvent was removed in vacuo to give a tan residue which was dissolved in a small volume of ether and purified by column chromatography on silica gel eluted with hexane/ether (4:1). After combination of the appropriate fractions, and removal of the solvent by evaporation, a white solid residue remained which was recrystallized from petroleum ether to afford methyl 17-(3-nitrophenyl)-16-heptadecanoate as white leaflets.

The methyl 17-(3-nitrophenyl)-16-heptadecanoate was reduced to the corresponding amino ester by catalytic hydrogenation, iodinated to obtain methyl 17-(3-amino-2,4,6-triiodophenyl)-heptadecanoate, and hydrolyzed to the corresponding carboxylic acid, 17-(3-amino-2,4,6-triiodophenyl)-heptadecanoic acid, by techniques similar to that described in Example 3.

Synthesis of 1,3-Disubstituted Triclyceride Analogs

Various techniques can be devised to synthesize 1,3-disubstituted triglyceride analogs in accordance with the invention herein. In one illustrative embodiment, shown as Method A on the flow chart shown in FIG. 2, such synthesis can be accomplished by diacylation of 1,3-dihydroxyacetone with an ω-(3-amino-2,4,6-triiodophenyl)-alkanoic acid, such as prepared in accordance with the illustrative examples given hereinabove. The resulting diacylated ketone is then reduced to the corresponding glyceryl-1,3-diester. Reaction of the glyceryl-1,3-diester with a naturally occuring fatty acid yields the final product, glyceryl-2-alkanoyl-1,3-di-ω-(3-amino-2,4,6-triiodophenyl)ester.

Examples 5 through 9 are directed to preparation of glyceryl-2-palmitoyl-1,3-di-ω-(3-amino-2,4,6-triiodophenyl)alkanoates of the general formula:

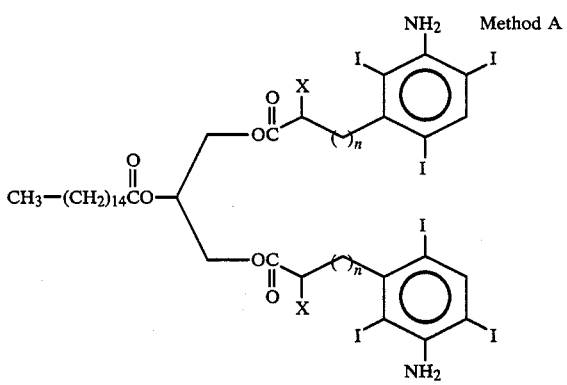

EXAMPLE 5

1,3-dihydroxyacetone was diacylated with ω-(3-amino-2,4,6-triiodophenyl)-iopanoic acid to produce 1,3-dihydroxypropan-2-one-1,3-di-(3-amino-2,4,6-triiodophenyl)-iopanoate by adding 9.8 g (47.5 mmol) of dicyclohexylcarbodiimide (DCC) to a rapidly stirring suspension of 1.97 g (21.9 mmol) of dihydroxyacetone dimer, 25 g (43.2 mmol) of the iopanoic acid, and a catalytic amount of 4-(dimethylamino)pyridine (DMAP)-in 120 ml of dry methylene chloride. The reaction mixture was stirred under $N_2$ for 66 hours, then diluted with an additional 200 ml dry methylene chloride, and filtered to remove any precipitated dicyclohexylurea (DCU). The filtrate was washed with 0.5 N HCl twice, with saturated aq. $NaHCO_3$, $H_2O$, and brine, and was dried with $MgSO_4$. The solvent was removed in vacuo to give a residue which was triturated with 100 ml of anhydrous ether to precipitate any remaining traces of DCU. The DCU was removed by filtration and the filtrate was placed in vacuo to remove the solvent. The resulting residue was crystallized from acetone to give the diacylated ketone as a white powder.

A stirred suspension of 4.3 g (3.6 mmol) of the diacylated ketone in a mixture of 30 ml THF, 8 ml benzene, and 2 ml $H_2O$, was cooled to 5° C. in an ice bath and treated with 204 mg (5.4 mmol) $NaBH_4$. The reaction mixture was stirred for an additional 30 minutes at 5° C. and treated with glacial acetic acid (0.3 ml) to destroy excess borohydride. The resulting solution was diluted with 250 ml $CH_2Cl_2$ and extracted with saturated aqueous $NH_4Cl$ twice, with water, and with brine, and then dried with $MgSO_4$. Removal of solvent in vacuo afforded semi-pure glyceryl-1,3-diiopanoate which was further purified by column chromatography on silica gel eluted with $CHCl_3$/hexane/ethyl acetate. Removal of the solvents from the appropriate chromatography fractions yielded purified glyceryl-1,3-diiopanoate as a yellowish amorphous solid which resisted recrystallization.

The triglyceride was created by adding 379 mg (1.84 mmol) DCC to a rapidily stirring solution 2.0 g.(1.67 mmol) of the alcohol produced in the prior step, 428 mg (1.67 mmol) of palmitic acid, and a catalytic amount of DMAP (20 mg) in 80 ml anhydrous $CH_2Cl_2$ which was kept under $N_2$. The reaction mixture was stirred for 66 hours, diluted with $CH_2Cl_2$ (200 ml) and filtered to remove precipitate DCU. The filtrate was washed successively with 0.5 N HCl twice, sat. aq. $NaHCO_3$ twice, water, and brine, and dried with $MgSO_4$. Removal of the solvent in vacuo yielded a yellow gum which resisted crystallization even after purification by column chromatography. The final product was glyceryl-2-palmitoyl-1,3-di-(3-amino-2,4,6-triiodophenyl)iopanoate.

EXAMPLE 6

12-(3-amino-2,4,6-triiodophenyl)-dodecanoic acid, as produced above in Example 3, was combined with dihydroxyacetone and DMAP in a solution of anhy. $CH_2Cl_2$ and treated with DCC in a manner similar to that described in Example 5. In particular, 180 mg (2.0 mmol) dihydroxyacetone, 2.68 g (4.0 mmol) of the dodecanoic acid, and 55 mg DMAP in 30 ml anhy. $CH_2Cl_2$ were treated with 908 mg (4.4 mmol) DCC. The reaction mixture was stirred for 18 hours to yield crude product which was purified by column chromatography on silica gel eluted with $CHCl_3$. Removal of the solvent in vacuo from the appropriate fraction yielded a white residue which was recrystallized from acetone/$CH_2Cl_2$ to yield 1,3-dihydroxypropan-2-one-1,3-di-12-(3-amino-2,4,6-triiodophenyl)-dodecanoate as a white powder.

1.45 g (1.04 mmol) of this ketone was dissolved in 15 ml THF, 3 ml benzene, and 0.5 ml water and treated with 59 mg (1.56 mmol) neutral NaBH₄ in the same manner as described in Example 5. The result was an off-white semi-solid which was recrystallized from acetone to give glyceryl-1,3-di-(3-amino-2,4,6-triiodophenyl)-dodecanoate as colorless flakes.

Treatment of 200 mg (0.14 mmol) of this alcohol, 55 mg (0.21 mmol) palmitic acid and 5 mg DMAP with 49 mg (0.24 mmol) DCC for 18 hours in the manner descried in Example 5 yielded crudei glyceryl-2-palmitoyl-1,3-di-12-(3-amino-2,4,6-triiodophenyl)-dodecanoate which was purified by column chromatography on silica gel eluted with hexane/ethyl acetate to produce an amorphous solid.

EXAMPLE 7

The 17-(3-amino-2,4,6-triiodophenyl)-heptadecanoic acid produced in Example 4 (400 mg, 0.53 mmol) was combined with 24 mg (0.26 mmol) dihydroxyacetone and 10 mg DMAP in 5 ml anhy. $CH_2Cl_2$ and treated with 121 mg (0.58 mmol) DCC. The reaction mixture was stirred and treated in a manner similar to that described in detail in Example 5. Following purification of the residue by column chromatography, 1,3-dihydroxypropan-2-one-1,3-di-17-(3-amino-2,4,6-triiodophenyl)-heptadecanoate was recrystallized from acetone/$CH_2Cl_2$ to yield a white powder.

268 mg (0.17 mmol) of this ketone was dissolved in 3 ml THF, 0.5 ml benzene, and 0.05 ml $H_2O$ and treated with 10 mg (0.26 mmol) NaBH₄ to yield a tan solid which was purified by column chromatography on silica gel eluted with hexane/ethyl acetate (4:1). Recrystallization from acetone resulted in an off-white powder which was glyceryl-1,3-di-17-(3-amino-2,4,6-triiodophenyl)-heptadecanoate.

Treatment of this alcohol with palmitic acid, DMAP, and DCC as described above results in the formation of glyceryl-2-palmitoyl-1,3-di-17-(3-amino-2,4,6-triiodophenyl)-heptadecanoate.

Method B

Figure 3:
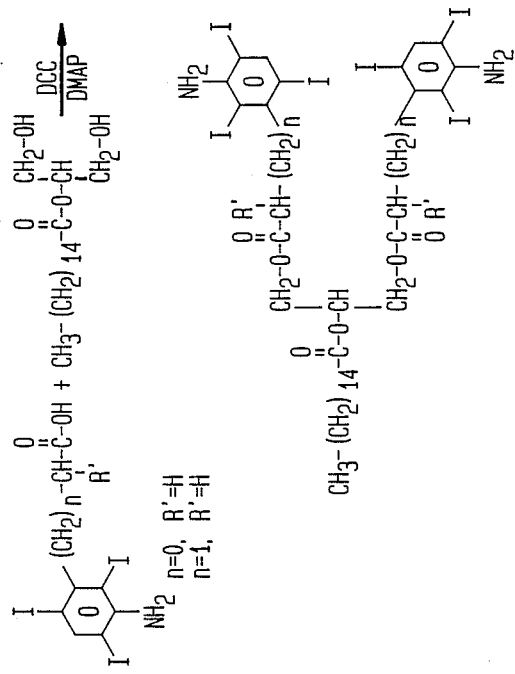
FIG. 3 is a flow chart of an alternative scheme for the synthesis of 1,3-disubstituted triglyceride analogs.

In an alternative embodiment of the invention, a 1,3-disubstituted triglyceride analog is synthesized by diacylation of 2-monopalmitin, an illustrative 2-substituted glycerol, with an ω-(3-amino-2,4,6-triiodophenyl)-alkanoic acid in accordance with the reaction sequence shown as Method B on FIG. 3. Examples 8 and 9 are directed to preparation of illustrative 1,3-disubstituted triglyceride analogs in accordance with this alternative embodiment.

EXAMPLE 8

Glyceryl-2-palmitoyl-1,3-di-2-(3-amino-2,4,6-triiodophenyl)acetate was synthesized from 3-(3-amino-2,4,6-triiodophenyl)acetic acid (Example 1) and 2-monopalmitin in the presence of a catalytic amount of DMAP and DCC. 1.15 g (2.2 mmol) of the acetic acid, 351 mg (1.0 mmol) 2-monopalmitin, and 30 mg DMAP were combined in 30 ml anhy. $CH_2Cl_2$ and treated with 500 m (2.4 mmol) DCC for 72 hours in the manner described above with respect to Examples 5–7. Recrystallization of the crude product in hexane/acetone at 26° C yielded glyceryl-2-palmitoyl-1,3-di-(3-amino-2,4,6-triiodophenyl)acetate as a white powder.

EXAMPLE 9

The 3-amino-2,4,6-triiodo-ohenylpropionic acid produced in accordance with Example 2 was likewise reacted with 2-monopalmitin to produce glyceryl-2-palmitoyl-1,3-di-3-(3-amino-2,4,6-triiodphenyl)-propionate. In particular, 1.14 g of the acid, 351 mg of 2-monopalmitin, 30 ml DMAP, and 477 mg DCC were reacted for 56 hours in the manner previously described. The resulting crude oil was purified by column chromatography on silica gel eluted with hexane/ethyl acetate (8:1). The white residue from the chromatography was recrystallized from hexane/ethyl acetate to yield the purified triglyceride analog as a white powder.

Synthesis of 1,2,3-trisubstituted Triglyceride Analogs

Figure 2:
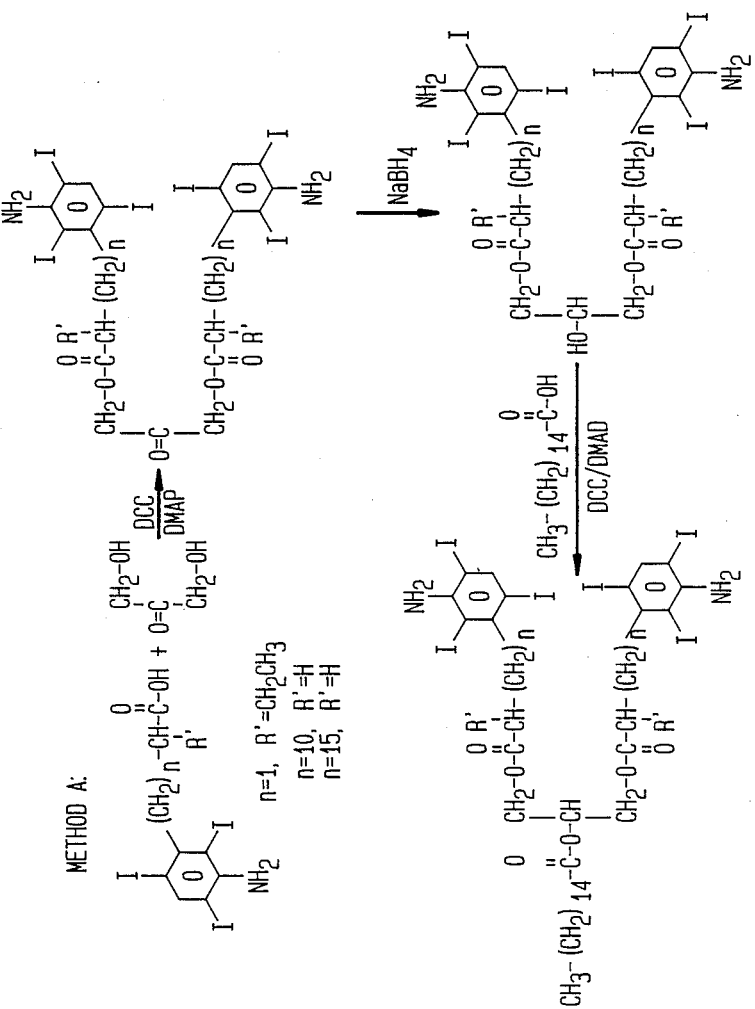
FIG. 2 is a flow chart of a scheme for the synthesis of 1,3-disubstituted triglyceride analogs.
Figure 4:
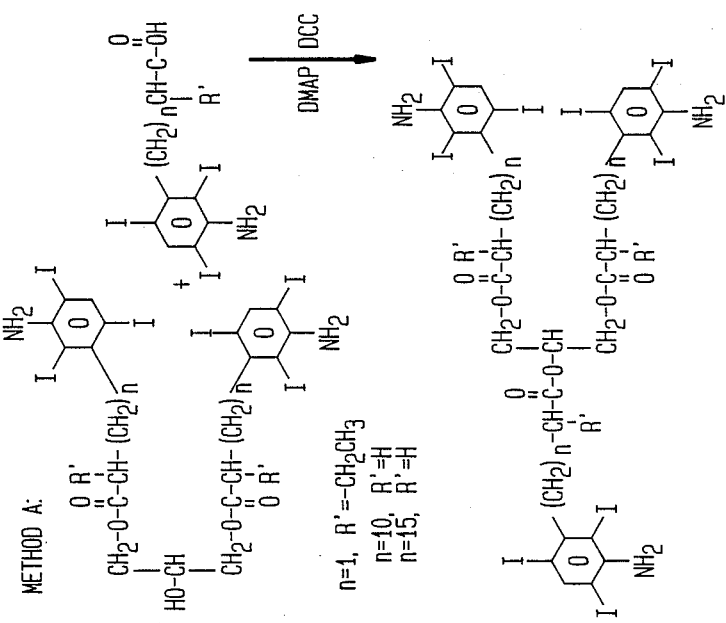
FIG. 4 is a flow chart of a scheme for the synthesis of 1,2,3-trisubstituted triglyceride analogs.

Preparation of 1,2,3-trisubstituted triglyceride analogs can be accomplished in the manner shown by the flow chart of FIG. 4. A diacylated alcohol, which can be produced in accordance with the Method A as shown in FIG. 2, is reacted with an ω-(3-amino-2,4,6-triiodophenyl-alkanoic acid to yield the desired 1,2,3-trisubstituted triglyceride analog.

Examples 10, 11, and 12 are directed to this method of synthesizing a 1,2,3-trisubstituted triglyceride. The basic method comprises treating a rapidly stirred suspension of the diacylalcohol (1.0 eq.), the acid (1.0–1.1 eq.) and a catalytic amount of DMAP (0.1 eq. in anhydrous $CH_2Cl_2$ (5 ml/mmol diacylalcohol) with DCC (1.1–1.2 eq.).

EXAMPLE 10

Glyceryl-1,2,3-triiopanoate was synthesized by treating 240 mg (0.2 mmol) of the diacylated alcohol, glyceryl-1,3-diiopanoate, such as produced in accordance with Example 5; 125 mg (0.22 mmol) ω-(3-amino-2,4,6-triiodophenyl)iopanoic acid; and 5 mg DMAP in $CH_2Cl_2$ with 50 mg (0.24 mmol) DCC. The resulting mixture was stirred under $N_2$ overnight at room temperature, diluted with $CH_2Cl_2$ and filtered to remove precipitated DCU. The filtrate was washed with 0.5 N HCl twice, with sat. aq. $NaHCO_3$ twice, with $H_2O$, and with brine, and dried with $MgSO_4$. The solvent was removed in vacuo and the remaining residue was purified by column chromatography on silica gel eluted with $CHCl_3$/ethyl acetate (4:1). Removal of the solvent in vacuo from the chromatography fractions left an off-white solid which was recrystallized in acetone/$CH_2Cl_2$ to yield glyceryl-1,2,3-triiopanoate as white nuggets.

EXAMPLE 11

200 mg (0.14 mmol) glyceryl-1,3-di-12-(3-amino-2,4,6-triiodophenyl)-dodecanoate as produced in Example 6 was combined with 105 mg (0.16 mmol) of 12-(3-amino-2,4,6-triiodophenyl)-dodecanoic acid as produced in Example 3 and 5 mg DMAP in $CH_2Cl_2$ and treated with 36 mg (0.17 mmol) DCC in the manner described above in Example 10. The crude reaction product was dissolved in a small amount of $CHCl_3$ and purified by column chromatography on silica gel eluted with $CHCl_3$. Removal of the solvent, followed by recrystallization from hexane/$CH_2Cl_2$ yielded glyceryl-1,2,3-tri-12-(3-amino-2,4,6-triiodophenyl)-dodecanoate.

EXAMPLE 12

A similar procedure was performed using 200 mg (0.13 mmol) glyceryl-1,3-di-17-(3-amino-2,4,6-triiodophenyl)-heptadecanoate as prepared in Example 7; 103 mg (0.14 mmol) 17-(3-amino-2,4,6-triiodophenyl)-heptadecanoic acid (Example 4); 3 mg DMAP and 31 mg (0.15 mmol) DCC in $CH_2Cl_2$ as previously described. Purification by column chromatography and subsequent recrystallization from acetone/$CH_2Cl_2$ yielded glyceryl-1,2,3-tri-17-(3-amino-2,4,6-triiodophenyl)-heptadecanoate as a white powder.

Figure 5:
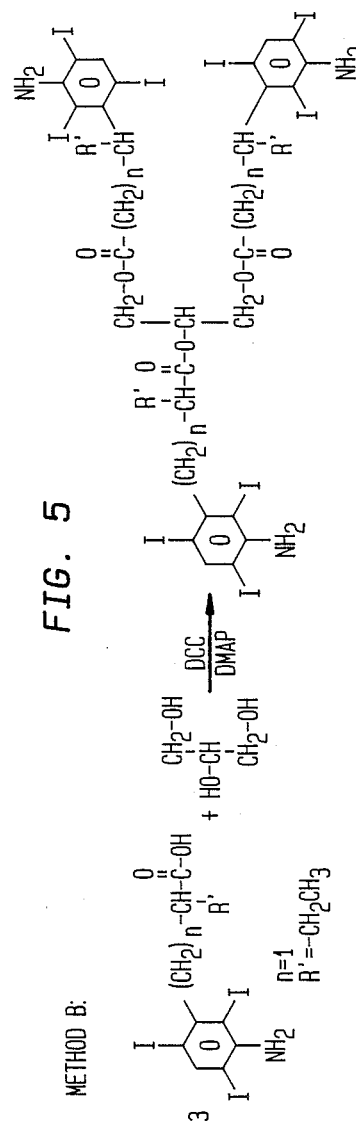
FIG. 5 is a flow chart of an alternative scheme for the synthesis of 1,2,3-trisubstituted triglyceride analogs.

In another illustrative embodiment of a reaction sequence for preparation of 1,2,3-trisubstituted triglyceride analogs, an ω-(3-amino-2,4,6-triiodophenyl)-alkanoic acid is reacted with glycerol as shown in the flow chart of FIG. 5 and described with more specificity in Example 13.

EXAMPLE 13

Glyceryl-1,2,3-tri-3-(3-amino-2,4,6-triiodophenyl)-propionate was synthesized as follows:

397 mg (1.9 mmol) DCC was added to a rapidly stirred suspension of 46 mg (0.5 mmol) glycerol, 951 mg (1.75 mmol) 3-amino-2,4,6-triiodophenylpropionic acid as produced in Example 2, and 24 mg DMAP in 10 ml anhydrous $CH_2Cl_2$. The reaction mixture was stirred under $N_2$ for 96 hours, diluted with $CH_2Cl_2$ (20 ml) and filtered to remove precipitated DCU and a yellow precipitate which was less polar than the DCC-acid adduct, but more polar than the free acid. The filtrate, however, did not contain the product. The filter cake was dissolved in anhydrous DMSO with heating to about 100° C. The yellow solution was then allowed to cool and the white needles which formed (DCU) were removed by filtration. The filtrate was placed under vacuum to remove the solvent at 100° C. The yellow residue which remained was dissolved in a small amount of THF and purified by column chromatography on silica gel eluted with hexane/ethyl acetate (1:1). Subsequent removal of the solvents in vacuo and crystallization from acetone/$CH_2Cl_2$ yielded the desired trisubstituted triglyceride as yellow nuggets.

Radioiodination of the Triglyceride Analogs

For certain uses, such as scintigraphy or experimental evaluation of tissue distribution, it is desirable to create radioactive compounds. Radioiodination of the polyiodinated triglyceride analogs disclosed herein can be accomplished by a variety of techniques, some of which are known in the art. For example, aromatic compounds with electron donating groups (such as anilines) can be radiolabeled by electrophilic iodination in the presence of radioiodine, iodine monochloride, chloramine-T, iodogen, etc. Unactivated aromatic rings, can be radioiodinated by exchange of a leaving group, such as aryl boronic acids, aryl thallium trifluoroacetates, triazenes, or metallated arenes with radioiodine. Direct electophilic radioiodination of a phenyl ring is yet another alternative, but may give rise to isomeric mixtures which are usually difficult to separate. Iodine exchange of aryl iodides with radio-iodide may be a preferable approach insofar as no complex separation techniques are necessary since the substrate and radioiodinated product are chemically identical.

In a preferred embodiment of the invention, an isotope exchange-type technique is utilized wherein the substrate and radioiodide are reacted at an elevated temperature in a "melt". The molten reaction medium possesses a sufficiently high dielectric constant to solubilize both the substrate and radioiodide. Examples of reaction media currently in use are benzoic acid (mp 122° C., bp 249° C.) and acetamide, (mp 82° C., bp 221° C.). In a specific preferred embodiment, an acidic exchange medium comprising pivalic acid, a homolog of acetic acid, also known as trimethylacetic acid, was used. Pivalic acid has a melting point of 33° C. and a boiling point of 164° C. The exchange reaction was essentially complete in about 1 hour at 155° C.

EXAMPLE 14

Iodine-125 was used as a no-carrier-added solution of $Na^{125}I$ (5 mCi/0.1 ml) in reductant-free 0.1 N NaOH obtained from DuPont NEN Research Products, Boston, Mass. Of course, other isotopes of iodine (e.g., $I^{123}$, $I^{131}$) can be used. For radiodiagnostic purposes in humans, $I^{123}$ is preferred due to its short half-life. The radioiodination procedures may be modified, as known by those of skill in the art, to compensate for the difference in half-life.

About 1–5 mg of the compound to be radioiodinated was placed in a 2 ml vial and sealed with a teflon-lined rubber septum and aluminum cap. THF was freshly distilled from LiAlH under Ar. 100 to 200 μl of the distilled THF and 10–50 μl aq. $Na^{125}I$ were added in succession via a microliter syringe, and the vial was gently swirled to dissolve the contents and ensure homogeneity. Inlet and outlet cannuli were inserted and a gentle stream of $N_2$ was applied to evaporate the solvents. About 5–20 mg of pivalic acid, which had been dried by azeotrope with toluene and distilled under $N_2$, was added to the solid residue. The vial was resealed and partially immersed in a preheated oil bath to a temperature in the range of 155°–160° C. The isotope exchange reaction generally required approximately between 1 and 2 hours to complete. When complete, the reaction vial was allowed to cool, and about 200 μl of the dry THF was added with a glass syringe. The vial was gently swirled to mix the contents. The contents of the vial were transferred to the top of a silica gel-60 column and eluted with the appropriate solvent system. A hexane/ethyl acetate (5:2) solvent was used for the ester/triglycerides and a THF/hexane (6:4) solvent was used for the acids. The $R_f$ of $Na^{125}I$, in either case, was from 0–0.05.

In certain embodiments, excess pivalic acid was removed prior to chromatography by inserting a disposable syringe containing granulated charcoal as a trap into the reaction vial while heating and allowing the pivalic acid to distill into the trap. This may be necessary when labeling polar compounds.

Although any of the polyiodinated triglyceride analogs pf the invention herein may be radioiodinated, it is not necessary for an iodophenyl substituent to the triglyceride backbone to be polyiodinated. For scintigraphic purposes, a monoiodinated substituent, appropriately radioiodinated, can achieve the desired results and may be preferred because it reduces the radioactive dose to the patient. Thus, a monoiodophenyl aliphatic chain may be substituted for the 3-substituted-2,4,6-triiodophenyl aliphatic chain.

The Carrier Vehicle

The above-described polyiodinated triglyceride analogs may be administered to mammalian subjects as radiologic agents by a known manner, such as intravenously. For hepatic imaging, intravenous injection is the technique of preference. A transport agent, or carrier vehicle, is required for the lipid-soluble radiologic agents disclosed herein. For the low doses of radiotagged agents required for nuclear medicine, a solution of albumin, for example, is suitable. For the larger doses require for radiologic contrast agents, a preferred embodiment of the invention utilizes a lipid emulsion as a vehicle for the radiologic agents.

A lipid emulsion would take advantage of the body's natural metabolic processes in a fashion similar to the way the polyiodinated triglyceride analogs disclosed herein do. In a preferred embodiment of the invention, the lipid emulsion has a lipid core packed with triglycerides and cholesteryl esters surrounded by a phospholipid monolayer containing traces of cholesterol for stability. Various apoproteins embedded in the monolayer are responsible for directing the complex to the target tissue. Triglycerides are transported in the plasma primarily by chylomicrons. The capacity to transport triglycerides makes chylomicrons, or chylomicron-like formulations, a preferred carrier vehicle for the polyiodinated triglyceride analogs of the invention herein.

Basically, the preferred carrier vehicle comprises a lipid emulsion containing about 10% triglycerides in a weight-to-volume ratio and a phospholipid monolayer of phosphatidyl choline stabilized with a sterol, such as cholesterol. The triglyceride portion comprises a mixture of polyiodinated triglyceride analog of the type disclosed herein and a naturally occurring triglyceride, such as triolein, tristearin, or tripalmitin. Table II, shown hereinbelow with respect to Example 15, shows illustrative formulations for the lipid emulsion carrier.

EXAMPLE 15

In a specific illustrative embodiment of the invention, glyceryl-2-palmitoyl-1,3-di-(3-amino-2,4,6-triiodophenyl)iopanoate, as synthesized in Example 5, was incorporated into a lipid emulsion.

A 10% lipid emulsion of this triglyceride analog (TGA) and a natural triglyceride, in this case, triolein (TO) was combined in selectable proportions with phosphatidyl choline and cholesterol in a centrifuge tube. Table II shows ratio of the lipid components expressed as percent weight per 100 ml solution.

TABLE II

| PHOSPHATIDYL CHOLINE | CHOLESTEROL | TO | TGA |
| --- | --- | --- | --- |
| 1.2 | 0.1 | 9.5 | 0.5 |
| 1.2 | 0.1 | 9.0 | 1.0 |
| 1.2 | 0.1 | 8.5 | 1.5 |
| 1.2 | 0.1 | 8.0 | 2.0 |
| 3.0 | 0.1 | 6.0 | 4.0 |

The lipid mixture was dissolved in 10 ml of peroxide-free diethyl ether and thoroughly mixed. The ether was evaporated under a stream of $N_2$ with gentle warming. The residue remaining was again dissolved in peroxide-free ether and transferred to a gas-tight Teflon syringe with an addition needle. The syringe was placed in a syringe pump set to deliver about 0.69 ml of the lipid solution per minute. The lipid solution was thus added to a stirred solution of 2.25% glycerol:distilled water on a weight to volume ratio. The glycerol solution was maintained at a temperature in the range of 37° C.-40° C. under a stream of $N_2$. When no further traces of the ether solvent were detected, the reaction flask was flushed with nitrogen, sealed, and stirred for a period of time, generally in the range of 1-1.5 hours, at 37° C.-4° C. The crude oil in water emulsion, thus obtained, was either subjected to sonification or homogenization to form the final lipid emulsion. The lipid emulsion resulting from either technique was then extruded through a 0.6μ Nucleopore polycarbonate membrane to remove large particles or lipid aggregates.

The lipid emulsion carrier formulations were assessed by gel permeation chromatography for size distribution and purity and were found to be uniform and free of extraneous materials. The particle size range was determined by negative-stain transmission electron microscopy and found to have a mean particle size of 92.2+4.4 nm and a uniform particle distribution of 366.7-25.9 nm (which compares favorably with chlylomicrons at 500-80 nm).

Evaluation of the TGA/lipid emulsion described hereinabove as a CT contrast agent was done by infusion of the last formulation on Table II into anesthetized New Zealand white rabbits. A dose in the range of 32-35 mgI/Kg body weight was used. Contiguous 0.5 cm thick axial CT scans were acquired from mid-thorax to mid-abdomen prior to and at selected intervals beginning 5 minutes after completion of the infusion. Scans were performed using either a GE CT/T 8800 or 9800 using targeted program with rapid scan sequences. The results showed enhanced liver attenuation of about 21 HU. Initial high contrast enhancement of the liver began between about 15-60 minutes post-infusion. However, maximum enhancement did not occur until somewhat later (up to two weeks).

It should be noted that choice of the appropriate vehicle for site-specific delivery would enable the polyiodinated triglyceride analogs of the invention to be used for contrast enhancement of other organs, such as the spleen, and to be used as a radiopaque in other techniques, such as lymphography.

Although the invention has been described in terms of specific embodiments and applications, persons skilled in this art can, in light of this teaching, generate additional embodiments without exceeding the scope or departing from the spirit of the claimed invention. In particular, the methods of synthesis are merely illustrative and can be modified by those of skill in the art for the production of various substituted triglyceride analogs in accordance with the invention. Moreover, other techniques of radio-tagging the analogs may be employed, as can other formulations for delivering the analogs to the target organ or cells. Accordingly, it is to be understood that the drawings and descriptions in this disclosure are proffered to facilitate comprehension of the invention and should not be construed to limit the scope thereof.

We claim:

1. A compound selected from the group consisting of triglycerides of the general formula:

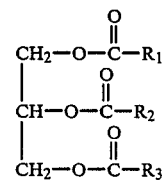

wherein $R_1$, $R_2$, and $R_3$ are each selected from the group consisting of saturated and unsaturated aliphatic hydrocarbon chains found in naturally occurring fatty acids, and iodophenyls of the general formula:

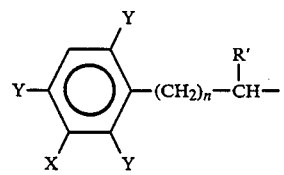

wherein X is selected from the group consisting of H, NH$_2$ and NHCOR″, R′ is selected from the group consisting of H and lower alkyls, R″ is a lower alkyl, n is an integer from 0–15, wherein at least two of said R$^1$, R$_2$, R$_3$ are said iodophenyls and wherein Y is selected from the group consisting of hydrogen or a radioactive isotope of iodine wherein at least one Y is a radioactive isotope of iodine.

2. The compound of claim 1 wherein said radioactive isotope of iodine is selected from the group consisting of $^{123}$I, $^{125}$I, and $^{131}$I.

3. The compound of claim 2 wherein R$_1$ and R$_3$ are selected to be said 3-substituted-2,4,6-triiodophenyls.

4. The compound of claim 1 wherein R$_1$ and R$_3$ are selected to be said iodophenyls.

5. The compound of claim 1 wherein R$_1$, R$_2$, and R$_3$ are selected to be said iodophenyls.

6. A compound selected from the group consisting of triglycerides of the general formula:

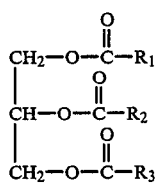

wherein R$^1$, R$_2$, and R$_3$ are each selected from the group consisting of saturated and unsaturated aliphatic hydrocarbon chains found in naturally occurring fatty acids, and are 3-substituted-2,4,6-triiodophenyls of the general formula:

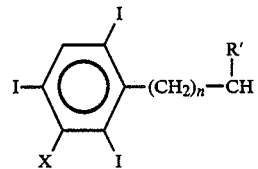

wherein X is selected from the group consisting of H, NH$_2$ and NHCOR″, R′ is selected from the group consisting of H and lower alkyls, R″ is a lower alkyl, n is an integer from 0–15, wherein at least two of said R$_1$, R$_2$, and R$_3$ are said 3-substituted-2,4,6-triiodophenyls and at least one of the iodines in said 3-substituted-2,4,6-triiodophenyls is a radioactive isotope of iodine.

7. The method of computed tomography visualtization of the liver which comprises administering to the body of a mammalian test subject an effective contrast-producing amount of a radiologic agent comprising the compound as described in claim 6 and detecting.

8. A method of scintigraphy imaging of the liver which comprises administering to the body of a mammalian test subject an effective radioactivity producing amount of a radiologic agent comprising the compound as described in claim 6 and detecting radioactivity.

9. The compound of claim 6 wherein said radioactive isotope of iodine is selected from the group consisting of $^{123}$I, $^{125}$I, and $^{131}$I.

10. The compound of claim 6 wherein R$_1$, R$_2$, and R$_3$ are selected to be said 3-substituted-2,4,6-triiodophenyls.

* * * * *